United States Patent
Mogna (10) Patent No.: US 11,628,193 B2
(45) Date of Patent: Apr. 18, 2023

(54) COMPOSITION OF LACTIC BACTERIA FOR USE IN THE TREATMENT OF INFECTIONS DUE TO PROPIONIBACTERIUM ACNES AND IN PARTICULAR FOR ACNE

(71) Applicant: Probiotical S.p.A., Novara (IT)

(72) Inventor: Giovanni Mogna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 720 days.

(21) Appl. No.: 15/750,484

(22) PCT Filed: Aug. 12, 2016

(86) PCT No.: PCT/IB2016/054869
§ 371 (c)(1),
(2) Date: Feb. 5, 2018

(87) PCT Pub. No.: WO2017/025936
PCT Pub. Date: Feb. 16, 2017

(65) Prior Publication Data
US 2019/0015463 A1 Jan. 17, 2019

(30) Foreign Application Priority Data
Aug. 13, 2015 (IT) .................. 102015000044669

(51) Int. Cl.
*A61K 35/747* (2015.01)
*A61P 17/10* (2006.01)
*A61P 17/08* (2006.01)

(52) U.S. Cl.
CPC ............ *A61K 35/747* (2013.01); *A61P 17/08* (2018.01); *A61P 17/10* (2018.01)

(58) Field of Classification Search
None
See application file for complete search history.

(56) References Cited

U.S. PATENT DOCUMENTS

| 2008/0107634 A1* | 5/2008 | Mogna ................. A61K 9/145 424/93.45 |
| 2009/0317370 A1* | 12/2009 | Lang .................... A61K 35/74 424/93.45 |
| 2011/0182861 A1 | 7/2011 | Castiel et al. |
| 2014/0065115 A1 | 3/2014 | Mogna et al. |
| 2014/0370107 A1 | 12/2014 | Mogna et al. |

FOREIGN PATENT DOCUMENTS

| EP | 1995307 | 11/2008 |
| JP | 2008539747 A | 11/2008 |
| WO | WO 98/10743 | 3/1998 |
| WO | WO 2010/013179 A1 | 2/2010 |
| WO | WO 2011/029784 | 3/2011 |
| WO | WO 2012/101500 A1 | 8/2012 |
| WO | WO 2014/096641 | 6/2014 |

OTHER PUBLICATIONS

Kanmani, P. et al. 2018. Genomic characterization of Lactobacillus delbrueckii TUA4408L and evaluation of the antiviral activities of its extracellular polysaccharides in porcine intestinal epithelial cells. Frontiers in Immunology 9: 1-16. specif. pp. 1, 2, 5, 6.*
Chularojanamontri, L. et al. May 2014. Moisturizers for acne. What are their constituents? Journal of Clinical and Aesthetic Dermatology 7(5): 36-44. specif. pp. 36, 38.*
Germond, J.-E. et al. 2003. Evolution of bacterial species Lactobacillus delbrueckii: a partial genomic study with reflections on prokaryotic species concept. Molecular Biology and Evolution 20(1): 93-104. specif. p. 93.*
Arihara et al., "Salivacin 140, a novel bacteriocin from *Lactobacillus salivarius* subsp. salicinius T140 active against pathogenic bacteria", Letters in Applied Microbiology, 1996, 22: 420-424.
Kang et al., "Effect of Lactobacillus reuteri on the Proliferation of Propionibacterium acnes and *Staphylococcus epidermidis*", The Journal of Microbiology, 2012, 50(1): 137-142.
Ou et al., "Heat-Killed Lactic Acid Bacteria Enhance Immunomodulatory Potential by Skewing the Immune Response toward Th1 Polarization", Journal of Food Science, 2011, 76(5): M260-267.
Chen et al., "Propionibacterium acnes-induced IL-8 production may be mediated by NF-kappaB activation in human monocytes", abstract, J. Dermatol Sci., 2002, 29(2): 97-103.

* cited by examiner

*Primary Examiner* — Renee Claytor
*Assistant Examiner* — Sharon M. Papciak
(74) *Attorney, Agent, or Firm* — James S. Keddie; Bozicevic, Field & Francis LLP (57) ABSTRACT

The present invention relates to selected strains of lactic bacteria for use in the treatment of infections caused by pathogenic bacteria belonging to the species *Propionibacterium acnes*, in particular for use in the preventive and/or curative treatment of dermatitis in general, seborrheic dermatitis, rosacea, eczema and acne. In addition, the present invention relates to a composition which comprises a mixture comprising or, alternatively, consisting of selected strains of lactic bacteria for use in the treatment of infections caused by pathogenic bacteria belonging to the species *Propionibacterium acnes*, in particular for use in the preventive and/or curative treatment of dermatitis in general, seborrheic dermatitis, rosacea, eczema and acne. The composition comprising said mixture of selected strains of lactic bacteria is formulated in a pharmaceutical form for oral use (novel food, supplement product or medical device or pharmaceutical composition) in the form of powder, dispersible powder, granulate, packets or stick, solution, spray solution, syrup, tablet, capsule, pill or lozenge; or for topical use (composition for medical device or pharmaceutical composition) in the form of cream, ointment, pomade, gel, hydrogel, dispersion, emulsion or spray to be used as such for skin applications, or for transdermal use even in the form of a band aid.

13 Claims, 4 Drawing Sheets

COMPOSITION OF LACTIC BACTERIA FOR USE IN THE TREATMENT OF INFECTIONS DUE TO PROPIONIBACTERIUM ACNES AND IN PARTICULAR FOR ACNE

CROSS-REFERENCE TO RELATED APPLICATIONS

This application is a § 371 national phase of International Application No. PCT/IB2016/054869, filed on Aug. 12, 2016, which claims the benefit of Italian Patent Application No. 102015000044669, filed on Aug. 13, 2015, which applications are incorporated by reference herein.

The present invention relates to selected strains of lactic bacteria for use in the treatment of infections and/or inflammations due to pathogenic bacteria belonging to the species *Propionibacterium acnes*, in particular for use in the preventive and/or curative treatment of dermatitis in general, seborrheic dermatitis, rosacea, eczema and acne. Furthermore, the present invention relates to a composition which comprises a mixture comprising or, alternatively, consisting of selected strains of lactic bacteria for use in the treatment of infections and/or inflammations caused by pathogenic bacteria belonging to the species *Propionibacterium acnes*, in particular for use in the preventive and/or curative treatment of dermatitis in general, seborrheic dermatitis, rosacea, eczema and acne. The composition comprising said mixture of selected strains of lactic bacteria is formulated in a pharmaceutical form for oral use (novel food, supplement product or medical device or pharmaceutical composition) in the form of powder, dispersible powder, granulate, packets or stick, solution, spray solution, syrup, tablet, capsule, pill or lozenge; or for topical use (composition for medical device or pharmaceutical composition) in the form of cream, ointment, pomade, gel, hydrogel, dispersion, emulsion or spray to be used as such for skin applications, or for transdermal use also in the form of band aid.

The term dermatitis is known to encompass a skin disease and, in general, consists of an inflammatory reaction of the skin, which appears as irritation. Seborrheic dermatitis (also referred to as seborrheic eczema) is a dermatitis primarily affecting areas of the body such as the scalp, the face, the chest and the ear canal. In particular, the skin areas rich in sebaceous glands are more likely to be affected. Seborrheic dermatitis can be sometimes confused and/or co-exist with rosacea. Rosacea is also known as a chronic dermatosis, namely, a pathological alteration of the skin, which usually involves the middle part of the face and appears as erythema and inflammatory acneiform eruptions, that is, with papules and pustules similar to acne. Since this latter characteristic, it was also referred in the past as "acne rosacea", a no longer used term in order to avoid confusion with acne.

Acne is known to be a skin disease characterized by an inflammatory process of the hair follicle and related sebaceous gland (commonly defined "pimple" or "furuncle"). The hair follicle is a particular structure of the skin (or cutis) producing the cells that will form the hair. The hair follicle is a bag-shaped introflexion of the epidermis with an enlargement at the base, called bulb, which continues with the neck getting narrowed up to the surface of the epidermis. The follicle forms, along with the hair and the related sebaceous gland, the pilosebaceous complex. The sebaceous gland, which is found in the skin and more precisely in the dermis underlying the epidermis, is deputed to the production and secretion of an oily substance called sebum (biological fluid), which mainly consists of cholesterol and fatty acids. The sebum serves to make the skin soft and hydrated, thus avoiding that it becomes dry. The areas of the body most affected by acne are the face, the neck, the shoulders, the back and the chest, in particular in Caucasian subjects from 12 to 20 years old. The most common kind of acne is called "acne vulgaris".

A still open challenge is to be able to treat dermatitis in general, seborrheic dermatitis, rosacea, eczema and acne in a natural way without the massive topical use of soaps or degreasing substances whether or not with topical or oral systemic antibiotic treatments. For example, using corticosteroids with anti-inflammatory activity for topical use.

Indeed, the use of soaps or degreasing substances is sometimes disadvantageous and is not devoid of limits and drawbacks. Although the skin, with an irritation caused for example by acne, seborrheic dermatitis, eczema or rosacea, is prone to be "fatty" due to a high presence of sebum, the undue degreasing action exerted by soaps and detergents, in fact, triggers an opposite effect whereby the skin, in order to protect itself, naturally increases its own sebum production. In addition, the undue removal of sebum can alter the hydrolipidic film favoring the bacterial colonization and increasing the skin sensitivity to potential irritants.

Therefore, the topical treatment with soaps or detergents of a skin affected by dermatitis in general, seborrheic dermatitis, rosacea, eczema or acne neither represents a decisive treatment nor can be stated to be an effective treatment for all the affected subjects.

On the other hand, the alternative to a topical treatment with soaps or detergents is represented by the typical strategy used by many dermatologists which, in order to curing skin diseases (dermatitis) such as for example acne, counteract the bacteria responsible for the infection by prescribing the use of topical or oral systemic antibiotics such as, for example, those based on tetracycline or minocycline, or derivatives thereof.

In the case of acne, for example, propioniform types of bacteria are responsible for the actual inflammation (response of the body) and infection occurring on the skin.

Bacteria belonging to the species *Propionibacterium acnes* are found in the skin or cutis surface and cause some skin diseases such as, for example, acne, among others. The acne, for example, occurs when bacteria, belonging to the species *Propionibacterium acnes*, clog the skin pores giving rise to an infection counteracted by the body (immune system) through inflammation of the skin itself.

As regards the pathogenesis of acne, the pathogenic microorganism *P. acnes* is stated to colonize the sebaceous gland ducts causing an innate immune response as well as the progression from a not-inflamed comedo to an inflamed papule, a pustule up to a nodule. Studies concerning inflammation due to *P. acnes* and facial lesions caused by acne show levels of IL-8 about 3015-fold greater (P<0.001) than adjacent areas of facial tissue free of acne ("*The role of inflammation in the pathology of acne*", (Literature Review) Emil A. Tanghetti MD Center for Dermatology and Laser Surgery, Sacramento, Calif.), September 2013, volume 6, number 9; "*Inflammation and Extracellular Matrix Degradation Mediated by Activated Transcription Factors Nuclear Factor-kB and Activator Protein-1 in inflammatory Acne Lesions in Vivo*", Sewon Kang et al, American Journal of Pathology, Vol. 166, No. 6, June 2005).

Chemokine IL-8 is often associated with inflammation and is increased by oxidative stress, thus resulting a key parameter for the localized inflammation: for this reason it was identified as the main proinflammatory mediator in acne.

Different strains of *P. acnes* were found to show a variable ability to induce the secretion of HBD2, IL-8 and IL-1alpha from keratinocytes ("*Pathways to inflammation: acne pathophysiology*" (Review article) Taylor M et al, EJD, vol. 21, no. 3, May-June 2011).

From the above, since the pathogenic microorganism *P. acnes* is responsible for processes causing the infection as well as those developing inflammation, which are both at the basis of acne, is desirable to have an effective treatment remedy (preventive and/or curative) of acne which is able to act against infection and, at the same time, against inflammation.

It was found that the use of specific topical or systemic antibiotics, acting against bacteria belonging to the species *Propionibacterium acnes*, could represent, but not always, a remedy for treating acne.

However, the use of topical (such as, for example, corticosteroids with anti-inflammatory activity for topical use) or systemic antibiotics fails in eliminating the cause underlying the mechanism by which propioniform bacteria elicit the onset of acne, or other diseases affecting the skin. In addition, the use of topical or systemic antibiotics is not devoid of side effects and contraindications, which strongly limit the use thereof, mainly when they are administered over extended periods of time. Furthermore, there is a problem due to the fact that the use of antibiotics develops a proved antibiotic resistance and the occurrence of resistant strains of *P. acnes*.

In this respect, the bacteriostatic, bactericidal and anti-inflammatory activity of some topical or systemic antibiotics has the disadvantage to cause the growth of strains of *P. acnes* resistant to some of the antimicrobials used in topical therapy (clindamycin, erythromycin, meclocycline and gentamicin).

Therefore, thus far, there is a need for being able to treat the pathogens responsible for infections eliciting skin inflammations or allergies.

Specifically, there is a need for having an effective and natural treatment for treating dermatitis, seborrheic dermatitis, eczema, rosacea and acne, so that to avoid or strongly reduce both the use of soaps or detergents and the use of topical or systemic antibiotics.

Therefore, there is still a strong need by operators for having a treatment against acne, which can be administered over long periods of time, in that is devoid of contraindications and side effects, and which is a decisive and effective treatment, acting both against infection by *P. acnes* and as a response to the unbalance caused to the immune system following to inflammation elicited by the pathogenic microorganism *P. acnes*.

The Applicant, after an intense and extended research and development activity, met the above-cited needs, succeeding to select and isolate specific strains of lactic bacteria, from a very large group of naturally occurring strains of bacteria. The selected strains of lactic bacteria are effective against the pathogen *P. acnes* responsible for some skin diseases such as, for example, acne, among others.

It is an object of the present invention at least a strain of bacteria belonging to the species *Lactobacillus salivarius* for use in the preventive and/or curative treatment of infections and/or inflammations caused by pathogenic bacteria belonging to the species *Propionibacterium acnes*, as claimed in the appended claims.

In a preferred embodiment, said at least a strain of bacteria belonging to the species *Lactobacillus salivarius* is isolated and identified as *Lactobacillus salivarius* LS03 (ID 1382)-DSM 22776 deposited on 23 Jul. 2009 at the Institute Deutsche Sammlung von Mikroorganismen and Zellkulturen GmbH (hereinafter DSMZ) by Probiotical SpA (Italy).

In another preferred embodiment, said at least a strain of bacteria belonging to the species *Lactobacillus salivarius* is isolated and identified as *Lactobacillus salivarius* LS04-DSM 24618 deposited on 2 Mar. 2011 at the Institute Deutsche Sammlung von Mikroorganismen and Zellkulturen GmbH (hereinafter DSMZ) by Probiotical SpA (Italy).

In still another preferred embodiment, said strain of bacteria is live or dead; preferably it can be in the form of tyndallized, sonicated, lysed cells, and/or fractions or enzymes and/or metabolites thereof.

In another preferred embodiment, said infections and/or inflammations caused by pathogenic bacteria belonging to the species *Propionibacterium acnes* are responsible for the onset of some skin or cutis diseases preferably selected from the group comprising or, alternatively, consisting of dermatitis, seborrheic dermatitis, eczema, rosacea and acne. Even more preferably, said disease is mild, moderate or chronic acne.

In another preferred embodiment, said pathogenic bacterium is *Propionibacterium acnes* ATCC 11827.

It is another object of the present invention, a composition comprising an effective amount of a mixture which comprises or, alternatively, consists of at least a strain of bacteria belonging to the species *Lactobacillus salivarius*, and a physiologically acceptable carrier; said composition being for use in the preventive and/or curative treatment of infections and/or inflammations caused by pathogenic bacteria belonging to the species *Propionibacterium acnes*.

In a preferred embodiment, said composition for use comprises said at least a strain of bacteria belonging to the species *Lactobacillus salivarius*, which was isolated and identified as *Lactobacillus salivarius* LS03 (ID 1382)-DSM 22776 deposited on 23 Jul. 2009 at DSMZ.

In another preferred embodiment, said composition for use comprises said at least a strain of bacteria belonging to the species *Lactobacillus salivarius*, which was isolated and identified as *Lactobacillus salivarius* LS04-DSM 24618 deposited on 2 Mar. 2011 at DSMZ.

In another embodiment, said composition for use comprises said at least a strain of bacteria belonging to the species *Lactobacillus salivarius* (*Lactobacillus salivarius* LS03 (ID 1382)-DSM 22776 and/or *Lactobacillus salivarius* LS04-DSM 24618), which can be live or dead; preferably it can be in the form of tyndallized, sonicated, lysed cells, and/or fractions or enzymes and/or metabolites thereof.

In another embodiment, said composition for use is active against both infections and inflammations caused by pathogenic bacteria belonging to the species *Propionibacterium acnes*, which are responsible for the onset of some skin or cutis diseases preferably selected from the group comprising or, alternatively, consisting of dermatitis, seborrheic dermatitis, eczema, rosacea and acne. Even more preferably said disease is mild, moderate or chronic acne.

In another embodiment, said composition for use is active against both infections and inflammations caused, for example, by the pathogenic bacterium *Propionibacterium acnes* ATCC 11827.

BRIEF DESCRIPTION OF THE DRAWINGS

FIG. 1 shows the results of a first soaked-disk inhibition test in which *Lactobacillus salivarius* LS01 (1797 S" and "1797 C"), DLV8 ("1813 C" and "1813 S"), and LS03 ("1382 C" and "1382 S"), and *Lactobacillus rhamnosus*

LR06 ("1697 C" and "1697 S"), LR04 ("1132 C" and "1132 S") and LR05 ("1602 C" and "1602 S") were assayed for their ability to inhibit the growth of *Propionibacterium acnes* ATCC 11827.

The Applicant tested 70 strains of bacteria for assessing their ability in modulating the activity of Th1 and Th2 lymphocytes. From a first screening, 22 of the 70 tested strains were found to have a remarkable anti-inflammatory activity (pro-Th2 strains). These 22 strains of bacteria were further studied for assessing their capability in inhibiting the release of chemokine IL-8. Chemokine IL-8 is often associated with inflammation and is increased by oxidative stress, thus resulting a key parameter for the localized inflammation: for this reason it was identified as the main proinflammatory mediator in acne.

The study showed that all the 22 strains of probiotic bacteria (Table 1) are able to significantly inhibit the release of IL-8 produced by PHA-activated PBMCs from 10 to 25%, such as BPS01 (DSM 26456) and LS04 (DSM 24618). In particular, 3 strains of probiotic bacteria: LDD01 (DSM 22106), LRE04 (DSM 23880) and LS03 (DSM 22776) are able to reducing the production of IL-8 leading to a reduction of 36%, 44% and 30%, respectively. Thus, the use of these probiotic strains, having a so remarkable action in the inhibition of IL-8, is obvious to be of primary relevance for limiting the proinflammatory activity of the chemokine at the site of inflammation and infection by *Propionibacterium acnes*.

It is an object of the present invention a strain of bacteria belonging to the species *Lactobacillus salivarius* for use in the preventive and/or curative treatment of infections and/or inflammations caused by pathogenic bacteria belonging to the species *Propionibacterium acnes*; said strain of bacteria belonging to the species *Lactobacillus salivarius* is isolated and identified as *Lactobacillus salivarius* LS04-DSM 24618 deposited on 2 Mar. 2011 at DSMZ by Probiotical SpA (Italy).

It is an object of the present invention a strain of bacteria belonging to the species *Lactobacillus delbrueckii* ssp. *delbrueckii* for use in the preventive and/or curative treatment of infections and/or inflammations caused by pathogenic bacteria belonging to the species *Propionibacterium acnes*; said strain of bacteria belonging to the species *Lactobacillus delbrueckii* ssp. *delbrueckii* is isolated and identified as *Lactobacillus delbrueckii* ssp. *delbrueckii* LDD01 (DSMZ 20074)-DSM 22106 deposited on 10 Dec. 2008 at DSMZ by Probiotical SpA (Italy).

It is an object of the present invention a strain of bacteria belonging to the species *Lactobacillus reuteri* for use in the preventive and/or curative treatment of infections and/or inflammations caused by pathogenic bacteria belonging to the species *Propionibacterium acnes*; said strain of bacteria belonging to the species *Lactobacillus reuteri* is isolated and identified as *Lactobacillus reuteri* LRE04-DSM 23880 deposited on 5 Aug. 2010 at DSMZ by Probiotical SpA (Italy).

It is an object of the present invention a strain of bacteria belonging to the species *Bifidobacterium pseudolongum* ssp. *globosum* for use in the preventive and/or curative treatment of infections and/or inflammations caused by pathogenic bacteria belonging to the species *Propionibacterium acnes*; said strain of bacteria belonging to the species *Bifidobacterium pseudolongum* ssp. *globosum* is isolated and identified as *Bifidobacterium pseudolongum* ssp. *globosum* BPS01-DSM 26456 deposited on 2 Oct. 2012 at DSMZ by Probiotical SpA (Italy).

It is an object of the present invention a composition comprising an effective amount of a mixture, which comprises or, alternatively, consists of:

(i) at least a strain of bacteria belonging to the species *Lactobacillus salivarius* selected from the group comprising or, alternatively, consisting of the strain *Lactobacillus salivarius* LS03-DSM 22776, the strain *Lactobacillus salivarius* LS04-DSM 24618 and/or mixtures thereof; and/or (ii) at least a strain of bacteria selected from the group comprising or, alternatively, consisting of the strain *Lactobacillus delbrueckii* ssp. *delbrueckii* LDD01 (DSMZ 20074)-DSM 22106, the strain *Lactobacillus reuteri* LRE04-DSM 23880 and/or the strain *Bifidobacterium pseudolongum* ssp. *globosum* BPS01-DSM 26456; and a physiologically acceptable carrier;

said composition being for use in the preventive and/or curative treatment of infections and/or inflammations caused by pathogenic bacteria belonging to the species *Propionibacterium acnes*. In an embodiment, said compositions for use of the present invention further comprise also an ammonium lactate, preferably of fermentative origin from lactic bacteria.

It is an object of the present invention a composition comprising an effective amount of a mixture, which comprises or, alternatively, consists of:

(i) at least a strain of bacteria belonging to the species *Lactobacillus salivarius* selected from the group comprising or, alternatively, consisting of the strain *Lactobacillus salivarius* LS03-DSM 22776; and/or (ii) at least a strain of bacteria selected from the group comprising or, alternatively, consisting of the strain *Lactobacillus delbrueckii* ssp. *delbrueckii* LDD01 (DSMZ 20074)-DSM 22106 and the strain *Lactobacillus reuteri* LRE04-DSM 23880; and a physiologically acceptable carrier; said composition being for use in the preventive and/or curative treatment of infections and/or inflammations caused by pathogenic bacteria belonging to the species *Propionibacterium acnes*. In an embodiment, said compositions for use of the present invention further comprise also an ammonium lactate, preferably of fermentative origin from lactic bacteria.

Advantageously, said mixture and, thus, said composition comprise or, alternatively, consist of:

a strain *Lactobacillus salivarius* LS03-DSM 22776; and/or a strain *Lactobacillus delbrueckii* ssp. *delbrueckii* LDD01 (DSMZ 20074)-DSM 22106; and a physiologically acceptable carrier;

said composition being for use in the preventive and/or curative treatment of infections and/or inflammations caused by pathogenic bacteria belonging to the species *Propioni-*

*bacterium acnes*. Said strains of bacteria are preferably in a weight ratio of about 1:1, or 2:1, or 3:1, or 4:1, or 5:1, 1:2. In an embodiment, said compositions for use of the present invention further comprise also an ammonium lactate, preferably of fermentative origin from lactic bacteria.

Advantageously, said mixture and, thus, said composition comprise or, alternatively, consist of:
  a strain *Lactobacillus salivarius* LS03-DSM 22776; and/or
  a strain *Lactobacillus reuteri* LRE04-DSM 23880; and a physiologically acceptable carrier;
  said composition being for use in the preventive and/or curative treatment of infections and/or inflammations caused by pathogenic bacteria belonging to the species *Propionibacterium acne*. Said strains of bacteria are preferably in a weight ratio of about 1:1, or 2:1, or 3:1, or 4:1, or 5:1, 1:2. In an embodiment, said compositions for use of the present invention further comprise also an ammonium lactate, preferably of fermentative origin from lactic bacteria.

Advantageously, said mixture and, thus, said composition comprise or, alternatively, consist of:
  a strain *Lactobacillus salivarius* LS03-DSM 22776; and
  a strain *Lactobacillus delbrueckii* ssp. *delbrueckii* LDD01 (DSMZ 20074)-DSM 22106; and
  a strain *Lactobacillus reuteri* LRE04-DSM 23880; and a physiologically acceptable carrier;
  said composition being for use in the preventive and/or curative treatment of infections and/or inflammations caused by pathogenic bacteria belonging to the species *Propionibacterium acnes*. Said strains of bacteria are preferably in a weight ratio of about 1:1:1, or 2:1:1, or 3:1:1, or 4:1:1, or 5:1:1, 1:2:1, or 1:1:2. In an embodiment, said compositions for use of the present invention further comprise also an ammonium lactate, preferably of fermentative origin from lactic bacteria.

The compositions of the present invention are effectively applied for use in the treatment of pimples or furuncles, preferably occurring in the face, shoulders, back, and upper part of the chest.

In said mixtures, said at least a strain of bacteria, or the combination of said strains of *Lactobacilli/Bifidobacteria* of the present invention, is in a total amount comprised from $1 \times 10^6$ to $1 \times 10^{12}$ CFU/g of mixture; preferably, from $1 \times 10^7$ to $1 \times 10^{11}$ CFU/g of mixture; more preferably, from $1 \times 10^8$ to $1 \times 10^{10}$ CFU/g of mixture. In an embodiment, said compositions for use of the present invention further comprise also an ammonium lactate, preferably of fermentative origin from lactic bacteria, in an amount comprised from 1 to 30% by weight, relative to the weight of the composition, preferably in an amount comprised from 5 to 15% by weight, relative to the weight of the composition.

In said compositions for use, said at least a strain of bacteria, or the combination of said strains of *Lactobacilli/Bifidobacteria* of the present invention, is in a total amount comprised from $1 \times 10^6$ to $1 \times 10^{11}$ CFU/g of composition; preferably, from $1 \times 10^7$ to $1 \times 10^{10}$ CFU/g of composition; more preferably, from $1 \times 10^8$ to $1 \times 10^6$ CFU/g of composition.

Said compositions for use can further comprise also the required/suitable amounts of co-formulants, excipients, carriers, surfactants, adjuvants, preservatives, coloring agents, as needed. Said substances are suitably quanti- and qualitatively selected among those known and commonly used by the pharmaceutical technician skilled in the formulation field.

The composition of the present invention comprising said mixture of selected strains of lactic bacteria is formulated in a pharmaceutical form for oral use (novel food, supplement product or medical device or pharmaceutical composition) in the form of powder, dispersible powder, granulate, packets or stick, solution, spray solution, syrup, tablet, capsule, pill or lozenge; or for topical use (composition for medical device or pharmaceutical composition) in the form of cream, ointment, pomade, gel, hydrogel, dispersion, emulsion or spray to be used as such for skin applications, or for transdermal use also in the form of band aid.

The above-cited strains of bacteria are in the mixture of the present invention in an amount comprised from 1% to 50% by weight, preferably from 5% to 40% by weight, even more preferably from 10% to 30%, relative to the total weight of the mixture. However, said percentage depends on the kind of the pharmaceutical form intended to be used. For example, in the case of capsules, the amount of said bacteria is greater than 25%, for example greater than 35%.

In an embodiment, the composition comprises strains of bacteria in a concentration comprised from $1 \times 10^6$ to $1 \times 10^{11}$ CFU/dose, preferably from $1 \times 10^8$ CFU/dose to $1 \times 10^1$ CFU/dose. The dose can be comprised from 0.2 to 10 g, for example can be 0.25 g, 1 g, 3 g, 5 g or 7 g. The strains of bacteria can be present in the composition in a solid form, for example in the form of powder, dry powder, or freeze-dried powder.

All the strains described and/or claimed in the present patent application were deposited according to the Budapest Treaty.

Experimental Part

1. Inhibition Tests for Bacterium *Propionibacterium acnes* ATCC 11827

Inhibition Tests for the Publicly available Bacterium *Propionibacterium acnes* ATCC 11827 were Conducted.

The intense research activity made by the Applicant focused on detecting, selecting and isolating one or more strains of lactic bacteria able to inhibiting the pathogenic bacterium belonging to the species *Propionibacterium acnes*.

For this reason, a large set of screening tests was set-up for a number of strains of bacteria belonging to the species *Lactobacillus salivarius* and *Lactobacillus rhamnosus*. The plate inhibition technique was used.

The pathogen *Propionibacterium acnes* (ATCC 11827) was used, by preparing a culture broth thereof. The pathogenic bacterium was grown in BHI (Brain Hearth Infusion) medium, supplemented with 1% glucose, up to a density of about 2 of McFarland's scale, and then diluted 1:10 in saline. Such a suspension was plated on Reimbold medium.

The Applicant started the experimental activity on a first large group of strains of bacteria belonging to the species *Lactobacillus salivarius* and *Lactobacillus rhamnosus* in order to obtain a second selected group of potential candidate strains. Next, the Applicant carried out a further selection and finally tested the following strains of bacteria, showing a remarkable activity against the target pathogenic strain:

*Lactobacillus salivarius* LS01 (ID 1797)-DSM 22775 deposited on 23 Jul. 2009 at DSMZ (*);

*Lactobacillus salivarius* DLV8 (ID 1813)-DSM 25545 deposited on 12 Jan. 2012 at DSMZ (*);

*Lactobacillus salivarius* LS03 (ID 1382)-DSM 22776 deposited on 23 Jul. 2009 at DSMZ (*);

*Lactobacillus rhamnosus* LR06 (ID 1697)-DSM 21981 deposited on 14 Nov. 2008 at DSMZ (*);

*Lactobacillus rhamnosus* LR04 (ID 1132)-DSM 16605 deposited on 20 Jul. 2004 at DSMZ by Anidral Srl (Italy), currently Probiotical SpA (Italy);

*Lactobacillus rhamnosus* LR05 (ID 1602)-DSM 19739 deposited on 27 Sep. 2007 at DSMZ by Anidral Srl (Italy), currently Probiotical SpA (Italy).

All the above (*) were deposited by Probiotical SpA (Italy).

Such bacteria were revitalized through two sequential inoculations in MRS broth, centrifuged and resuspended in fresh medium (v/v), indicated as C. The supernatant was neutralized and filtered, indicated as S.

Figure 1:
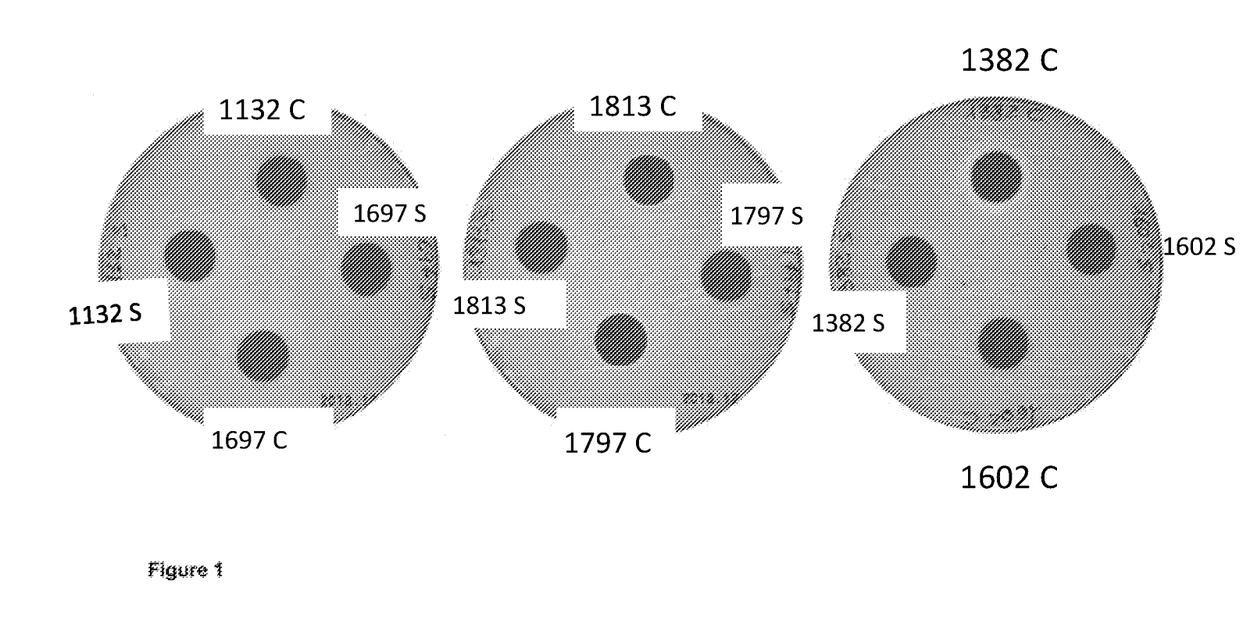

The inhibition test was then carried out by the soaked-disk technique as shown in FIG. 1.

The above test immediately showed a surprising and greater inhibition ability of the strain *Lactobacillus salivarius* LS03 (ID 1382)-DSM 22776 deposited on 23 Jul. 2009 at DSMZ against the target pathogenic strain.

Said inhibition activity is due to the ability of the strain *Lactobacillus salivarius* LS03 (ID 1382)-DSM 22776 deposited on 23 Jul. 2009 at DSMZ to producing bacteriocins very active against the pathogen *P. acnes*. It can reasonably be excluded that only an effect due to the acidity and/or the possible production of hydrogen peroxide occurs. The former reason is not contemplated since the other bacteria having similar acidifying activities had no effect on the growth of the target pathogen; the second reason is not contemplated since plate incubation occurred under anaerobiosis, a condition impeding the formation of hydrogen peroxide by lactobacilli.

Based on this result, the study was extended to other possible candidates, and the obtained result was further confirmed with the strain *Lactobacillus salivarius* LS03 (ID 1382)-DSM 22776 deposited on 23 Jul. 2009 at DSMZ.

Next, the following strains of bacteria were tested in a second test:

*Lactobacillus reuteri* LRE 01 (ID 1775)-DSM 23877 deposited on 5 Aug. 2010 at DSMZ;

*Lactobacillus reuteri* LRE 02 (ID 1774)-DSM 23878 deposited on 5 Aug. 2010 at DSMZ;

*Lactobacillus reuteri* LRE 03 (ID 1777)-DSM 23879 deposited on 5 Aug. 2010 at DSMZ;

*Lactobacillus reuteri* LRE 04 (ID 1779)-DSM 23880 deposited on 5 Aug. 2010 at DSMZ;

*Lactobacillus reuteri* LRE 05 (ID 1807)-DSM 25139 deposited on 2 Sep. 2011 at DSMZ.

All the above were deposited by Probiotical SpA (Italy).

Since in literature some *Streptococci thermophilus* were found to be able to produce broad-spectrum bacteriocins, we also included in the test some of the strains of bacteria belonging to the species *S. thermophilus*:

*Streptococcus thermophilus* YO 2 (1427)-DSM 16590 deposited on 20 Jul. 2004 at DSMZ;

*Streptococcus thermophilus* YO 3 (1286)-DSM 16591 deposited on 20 Jul. 2004 at DSMZ;

*Streptococcus thermophilus* YO 4 (1288)-DSM 16592 deposited on 20 Jul. 2004 at DSMZ;

*Streptococcus thermophilus* YO 5 (1405)-DSM 16593 deposited on 20 Jul. 2004 at DSMZ.

All the above were deposited by Anidral Srl (Italy), currently Probiotical SpA (Italy).

Figure 2:
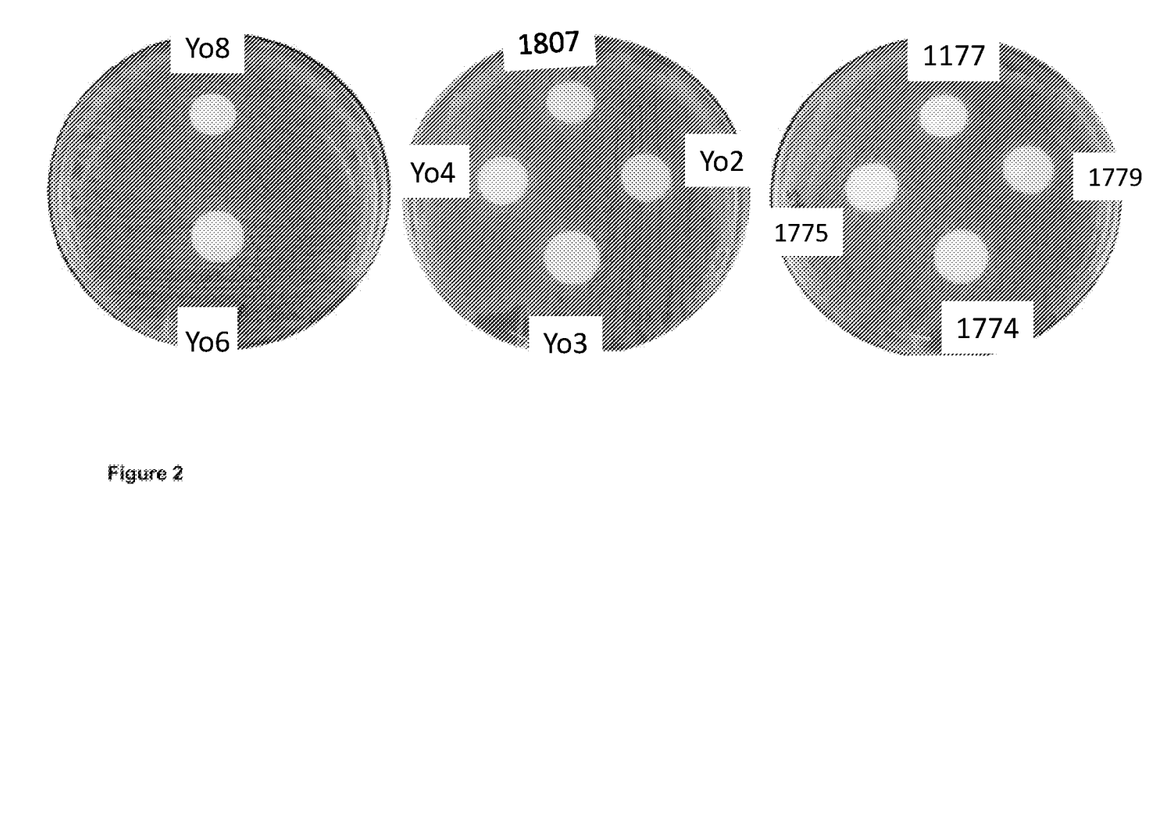
FIG. 2 shows the results of a second soaked-disk inhibition test in which *Lactobacillus reuteri* strains LRE 01 ("1775"), LRE 02 ("1774"), LRE 03 ("1777"), LRE 04 ("1779") and LRE 05 ("1807") and *Streptococcus thermophilus* strains YO 2 ("Yo2"), YO 3 ("Yo3"), YO 4 ("Yo4"), YO 5 ("Yo5"), YO 6 ("Yo6") and YO 8 ("Yo8") were assayed for their ability to inhibit the growth of *Propionibacterium acnes* ATCC 11827.

We carried out the screening of the bacterial resuspensions as described in the first experiment, thus obtaining the following results as shown in FIG. 2.

In this second screening of the strains, no useful results were obtained, further confirming the exceptional nature of the bacteriocin activity of the strain of the present invention LS03.

Then, a new test with the strain LS03 was conducted, in order to corroborate such an inhibition activity against the target pathogenic strain.

This second test served as a comparison with the strain *Lactobacillus rhamnosus* T12 (ID 1738) LMG P-25211 (WO2011/029784) as positive control, being part of a commercially available anti-acne formulation called Lichtena Norma-Acn®.

After growing the strains of bacteria, as described in the first test, the broth cultures were divided into two aliquots; a first broth culture aliquot was neutralized prior to the supernatant removal by centrifugation; whereas the other second aliquot was first centrifuged and than the supernatant only was neutralized.

In literature some bacteriocins in fact were found to adhere or not to the cell membrane of the pathogen depending on the acidic pH.

Figure 3:
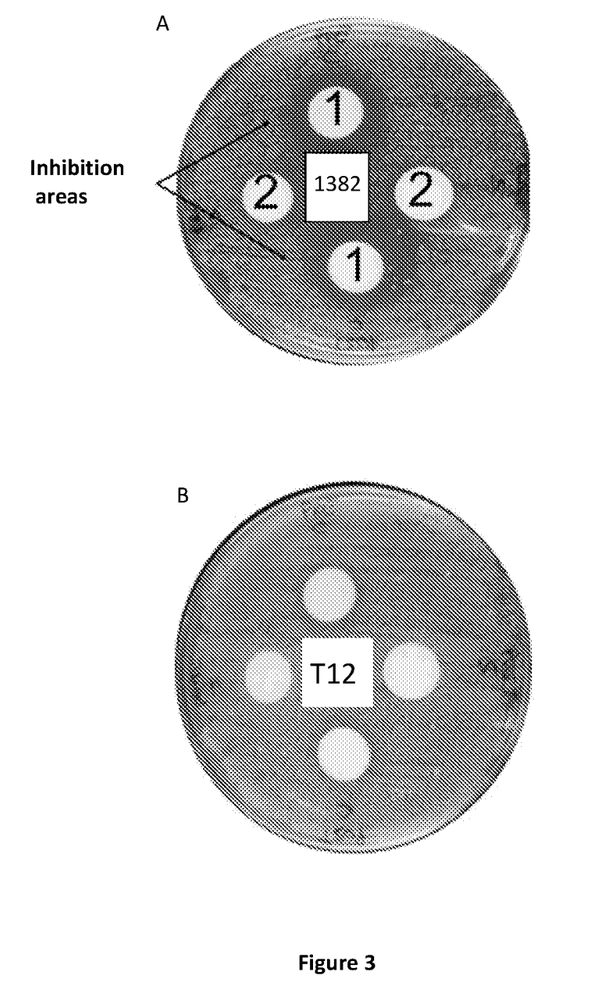
FIG. 3 shows the results of a third soaked-disk inhibition test in which *Lactobacillus salivarius* LS03 ("1382") and *Lactobacillus rhamnosus* T12 ("T12") were assayed for their ability to inhibit the growth of *Propionibacterium acnes* ATCC 11827.

The tested samples were thus 4 for either of the two tested strains: (*Lactobacillus rhamnosus* T12 (ID 1738) LMG P-25211 and *Lactobacillus salivarius* LS03 (ID 1382)-DSM 22776). Results are shown in FIG. 3.

Again, the strain *Lactobacillus salivarius* LS03 (ID 1382)-DSM 22776 deposited on 23.07.2009 at DSMZ exhibits a better inhibition ability than the strain *Lactobacillus rhamnosus* T12 LMG P-25211 (Lichtena) Norma-Acn® used as control.

The bacteriocin produced by the strain of bacteria LS03 shows adhesive abilities depending on the pH and, thus, is able to exert its inhibitory action in different contexts. The activity in an acidic environment alone would not be completely useful.

2. Assessment of the Ability of Probiotic Strains to Inhibit the IL-8 Release in PBMCs (Peripheral Blood Mononuclear Cells)

2.1 Aim

In this study 70 strains of probiotic bacteria were tested for assessing their ability in modulating the activity of lymphocytes Th1 and Th2. From a first screening of the 70 tested strains, 22 of them (Table 1) were found to have a remarkable anti-inflammatory activity (pro-Th2 strains).

Figure 4:
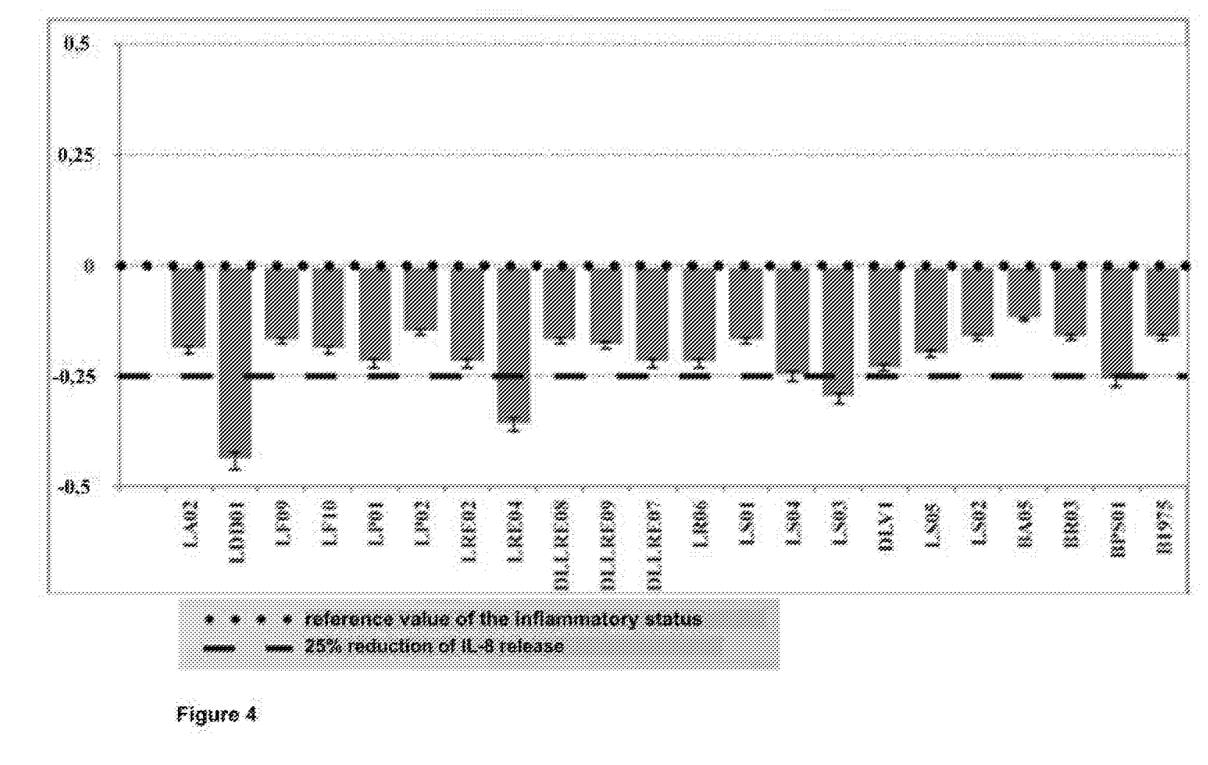
FIG. 4 is a bar chart showing the results of an IL-8 inhibition assay in which various strans were tested for their ability to inhibit the release of the chemokine IL-8 from peripheral blood mononuclear cells.

These 22 strains of probiotic bacteria (Table 1) were further studied for assessing their ability in inhibiting the release of chemokine IL-8 (FIG. 4). Chemokine IL-8 is often associated with inflammation and is increased by oxidative stress, thus resulting a key parameter for the localized inflammation: for this reason it was identified as the main proinflammatory mediator in acne.

In this study the ability of selected strains of probiotic bacteria (Table 1) in inhibiting the release of IL-8 by PBMCs was analyzed. IL-8 is a typical proinflammatory chemokine overproduced in acne.

TABLE 1

PRO-TH2 STRAINS LISTING

| NAME | Commercial abbreviation | Deposit number | Deposit date |
|---|---|---|---|
| *Lactobacillus acidophilus* | LA02 | DSM 21717 | 6 Aug. 2008 |
| *Lactobacillus delbrueckii* ssp. *delbrueckii* | LDD01 | DSM 22106 | 10 Dec. 2008 |
| *Lactobacillus fermentum* | LF09 | DSM 18298 | 24 May 2006 |
| *Lactobacillus fermentum* | LF10 | DSM 19187 | 20 Mar. 2007 |
| *Lactobacillus plantarum* 476LL 20 bi | LP01 | LMG P-21021 | 16 Oct. 2001 |

TABLE 1-continued

PRO-TH2 STRAINS LISTING

| NAME | Commercial abbreviation | Deposit number | Deposit date |
|---|---|---|---|
| Lactobacillus plantarum 776/1 bi | LP02 | LMG P-21020 | 16 Oct. 2001 |
| Lactobacillus reuteri | LRE02 | DSM 23878 | 5 Aug. 2010 |
| Lactobacillus reuteri | LRE04 | DSM 23880 | 5 Aug. 2010 |
| Lactobacillus reuteri | DLLRE08 | DSM 25684 | 16 Feb. 2012 |
| Lactobacillus reuteri | DLLRE09 | DSM 25685 | 16 Feb. 2012 |
| Lactobacillus reuteri | DLLRE07 | DSM 25683 | 16 Feb. 2012 |
| Lactobacillus rahmnosus | LR06 | DSM 21981 | 14 Nov. 2008 |
| Lactobacillus salivarius | LS01 | DSM 22775 | 23 Jul. 2009 |
| Lactobacillus salivarius | LS04 | DSM 24618 | 2 Mar. 2011 |
| Lactobacillus salivarius | LS03 | DSM 22776 | 23 Jul. 2009 |
| Lactobacillus salivarius | DLV1 | DSM 25138 | 2 Sep. 2011 |
| Lactobacillus salivarius | LS05 | DSM 26036 | 6 Jun. 2012 |
| Lactobacillus salivarius | LS02 | DSM 32204 | 13 Nov. 2015 |
| Bifidobacterium adolescentis EI-18 | BA05 | DSM 18352 | 15 Jun. 2006 |
| Bifidobacterium breve | BR03 | DSM 16604 | 20 Jul. 2004 |
| Bifidobacterium pseudolongum ssp. globosum | BPS01 | DSM 26456 | 2 Oct. 2012 |
| Bifidobacterium longum | B1975 | DSM 24709 | 7 Apr. 2011 |

2.2 Method: PBMC Stimulation

Isolating PBMCs from peripheral blood of healthy subjects according to protocol FICOLL.

Pre-incubating PBMCs with PHA (phytohemagglutinin) 1 μg/ml for 1 hour.

Stimulating PBMCs with the probiotic strains for 24 hours.

Collecting supernatants after centrifugation at 10000 rpm for 5 minutes and storing at −80° C. until use.

Assessing the IL-8 release with the E.L.I.S.A. kit (eBioscience, Human IL-8 ELISA Ready-Set-Go, 2nd generation).

Analyzing the data and statistical assessing carried out with a paired t-test, data are considered significant for $p<0.05$ values.

2.3 Method: ELISA Protocol for Assessing IL-8

Plate coating with 1× Coating Buffer, incubating at 4° C. overnight;

Washing with Wash Buffer (3×);

Dispensing 1× Blocking Buffer in each well and incubating for 1 hour at room temperature;

Washing with Wash buffer (1×);

Dispensing the samples and standard curve and incubating for 2 hours at room temperature;

Washing with Wash Buffer (5×);

Dispensing in each well the Detection Antibody Buffer and incubating for 1 hour at room temperature;

Washing with Wash Buffer (5×);

Dispensing in each well Avidin-HRP Buffer and incubating for 30 minutes at room temperature;

Washing with Wash Buffer (7×);

Incubating for 15 minutes with 1×TMB Solution and interrupting with Stop Solution;

Spectrophotometric reading at 450 nm.

2.4 Results: results for the chemokine IL-8 assay after 1-hour pre-stimulation with PHA followed by 24-hour incubation with selected strains of probiotic bacteria Th2 (Table 1) and subsequent assessment with the technique ELISA are shown in FIG. 4.

In FIG. 4, the value "0" (zero) relates to the reference value of the inflammatory status. Basically, it represents the PHA-activated cells. It is the stimulus of choice for the IL-8 release (it represents the maximum production of IL-8=positive control). Whereas the value "−0.25%" represents a reduction of 25% of IL-8 release.

2.5 Conclusions

From the study, all the 22 strains of probiotic bacteria (Table 1) were found to be able to significantly inhibit the release of IL-8 produced by PHA-activated PBMCs from 10 to 25%, such as BPS01 (DSM 26456) and LS04 (DSM 24618). In particular, 3 strains of probiotic bacteria: LDD01 (DSM 22106), LRE04 (DSM 23880) and LS03 (DSM 22776) are able to reducing the IL-8 production achieving a reduction equal to 36%, 44% and 30%, respectively.

It is thus obvious that the use of these probiotic strains, with a so remarkable action in inhibiting IL-8 has a fundamental relevance for limiting the proinflammatory action of chemokine in the site of inflammation and infection by *Propionibacterium acnes*.

Biological Deposits

*Lactobacillus salivarius* LS03 (ID 1382) was deposited at the Leibniz Institute DSMZ-German Collection of Microorganisms and Cell Cultures (DSMZ) as accession number DSM 22776 on Jul. 23, 2009;

*Lactobacillus salivarius* LS04 was deposited at the DSMZ as accession number DSM 24618 on Mar. 2, 2011;

*Lactobacillus delbrueckii* ssp. *delbrueckii* LDD01 (DSMZ 20074) was deposited at the DSMZ as accession number DSM 22106 on Dec. 10, 2008;

*Lactobacillus reuteri* LRE04 was deposited at the DSMZ as accession number DSM 23880 on Aug. 5, 2010, and

*Bifidobacterium pseudolongum* ssp. *globosum* BPS01 was deposited at the DSMZ as accession number DSM 26456 on Oct. 2, 2012.

The address of the DSMZ is: Leibniz Institute, Inhoffenstraβe 7B 38124 Braunschweig, Germany.

The invention claimed is:

1. A method for treating inflammation caused by pathogenic bacteria belonging to the species *Propionibacterium acnes*, comprising administering an effective amount of a composition comprising *Lactobacillus salivarius* LS03 (ID 1382) (deposited at the DSMZ as DSM 22776) to a patient.

2. The method of claim 1, wherein the composition comprises live bacterial cells.

3. The method of claim 1, wherein the patient has a skin or cutis disease.

4. The method of claim 3, wherein said skin or cutis disease is acne.

5. The method of claim 3, wherein the patient has a skin or cutis disease selected from the group consisting of dermatitis, seborrheic dermatitis, eczema, rosacea, and acne.

6. The method of claim 1, wherein said pathogenic bacterium is *Propionibacterium acnes* ATCC 11827.

7. The method of claim 1, wherein the composition comprises dead bacterial cells.

8. A method for treating inflammation caused by pathogenic bacteria belonging to the species *Propionibacterium*

*acnes*, comprising administering to a patient a composition comprising an effective amount of a mixture of bacteria and a physiologically acceptable carrier, wherein the mixture of bacteria comprises:

(i) *Lactobacillus salivarius* LS03 (deposited at the DSMZ as DSM 22776); and (ii) at least a strain of bacteria selected from the group consisting of the strain *Lactobacillus delbrueckii* ssp. *delbrueckii* LDD01 (deposited at the DSMZ as DSM 22106), the strain *Lactobacillus reuteri* LRE04 (deposited at the DSMZ as DSM 23880), and/or the strain *Bifidobacterium pseudolongum* ssp. *globosum* BPS01 (deposited at the DSMZ as DSM 26456).

9. The method of claim 8, wherein said composition further comprises ammonium lactate.

10. The method of claim 8, wherein the patient has pimples or furuncles.

11. The method of claim 8, wherein the mixture of bacteria comprises live bacterial cells.

12. The method of claim 8, wherein the strain of *Lactobacillus salivarius* LS03 and the strain of *Lactobacillus delbrueckii* ssp. *delbrueckii* LDD01 are, respectively, in a weight ratio of about 1:1, or 2:1, or 3:1, or 4:1, or 5:1, or 1:2.

13. The method of claim 8, wherein the strain of *Lactobacillus salivarius* LS03 and the strain of *Lactobacillus reuteri* LRE04 are, respectively, in a weight ratio of about 1:1, or 2:1, or 3:1, or 4:1, or 5:1, or 1:2.

\* \* \* \* \*